US012746398B2

(12) United States Patent
English

(10) Patent No.: US 12,746,398 B2
(45) Date of Patent: Sep. 29, 2026

(54) PCBA X-RAY ID TAG

(71) Applicant: Cardiac Pacemakers, Inc., St. Paul, MN (US)

(72) Inventor: James Michael English, Cahir (IE)

(73) Assignee: Cardiac Pacemakers, Inc., St. Paul, MN (US)

( * ) Notice: Subject to any disclaimer, the term of this patent is extended or adjusted under 35 U.S.C. 154(b) by 206 days.

(21) Appl. No.: 18/409,296

(22) Filed: Jan. 10, 2024

(65) Prior Publication Data

US 2024/0238601 A1 Jul. 18, 2024

Related U.S. Application Data

(60) Provisional application No. 63/439,222, filed on Jan. 16, 2023.

(51) Int. Cl.
*A61N 1/375* (2006.01)

(52) U.S. Cl.
CPC .................................. *A61N 1/375* (2013.01)

(58) Field of Classification Search
None
See application file for complete search history.

(56) References Cited

U.S. PATENT DOCUMENTS

| | | | | |
|---|---|---|---|---|
| 2012/0065503 A1* | 3/2012 | Rogers | A61B 90/39 | |
| | | | 600/431 | |
| 2018/0085593 A1* | 3/2018 | Fayram | A61N 1/0551 | |
| 2020/0121417 A1* | 4/2020 | Prescott | A61B 90/90 | |

* cited by examiner

*Primary Examiner* — Michael W Kahelin
(74) *Attorney, Agent, or Firm* — Nelson Mullins Riley & Scarborough LLP

(57) ABSTRACT

An implantable medical device includes a metal case having a hermetic seal; and an identification (ID) tag arranged within the sealed metal case, wherein the ID tag is readable by X-raying the device.

11 Claims, 7 Drawing Sheets

PCBA X-RAY ID TAG

CLAIM OF PRIORITY

This application claims the benefit of U.S. Provisional Application No. 63/439,222 filed on Jan. 16, 2023, which is hereby incorporated by reference in its entirety.

TECHNICAL FIELD

This patent application relates to ambulatory medical devices and, in particular, to identification (ID) tags for implantable medical devices.

BACKGROUND

It can be useful to uniquely identify a medical device. Implantable medical devices generally include a hermetically sealed metal case or metal housing, and an implantable medical device is typically hidden from view when implanted. It can be challenging to provide a way to uniquely identify an implantable medical device.

SUMMARY

Systems and methods are disclosed that relate to identification tags for implantable medical devices. Example 1 includes subject matter (such as an implantable medical device) including a metal case having a hermetic seal, and an identification (ID) tag arranged within the sealed metal case. The ID tag is readable by X-raying the implantable medical device.

In Example 2, the subject matter of Example 1 optionally includes an ID tag that includes tungsten, and a metal case that includes titanium.

In Example 3, the subject matter of one or both of Examples 1 and 2 optionally includes an ID tag that is a metal plate with alphanumeric characters cut out of the metal plate.

In Example 4, the subject matter of one or any combination of Examples 1-3 optionally includes a printed circuit board (PCB) disposed within the metal case, and the ID tag is glued to the PCB.

In Example 5, the subject matter of Example 4 optionally incudes a PCB that includes FR4 epoxy, and the ID tag is a metal ID tag that includes tungsten.

In Example 6, the subject matter of one or any combination of Examples 1-5 optionally includes a printed circuit board (PCB) disposed within the metal case, and an ID tag attached to the PCB without solder.

In Example 7, the subject matter of one or any combination of Examples 1-6 optionally includes the metal case and the ID tag being included in a leadless implantable medical device.

Example 8 includes subject matter (such as a method of forming an implantable medical device) or can optionally be combined with one or any combination of Examples 108 to include such subject matter, including forming a printed circuit board (PCB), disposing an ID tag on the PCB, and disposing the PCB in a metal case and sealing the metal case. The ID tag is readable within the metal case when X-raying the device.

In Example 9, the subject matter of Example 8 optionally includes forming the ID tag as a metal plate that includes tungsten and wherein disposing the ID tag in the metal case includes disposing the ID tag in a titanium metal case.

In Example 10, the subject matter of one or both of Examples 8 and 9 optionally includes forming the ID tag by cutting alphanumeric characters out of the metal plate.

In Example 11, the subject matter of one or any combination of Examples 8-10 optionally includes surface mounting the ID tag on the PCB using glue.

In Example 12, the subject matter of one or any combination of Examples 8-11 optionally includes re-flowing the PCB after disposing the ID tag on the PCB.

In Example 13, the subject matter of one or any combination of Examples 8-12 optionally includes glue-dot surface mounting of the ID tag on the PCB.

In Example 14, the subject matter of one or any combination of Examples 8-13 optionally includes surface mounting the ID tag on the PCB without soldering the ID tag.

In Example 15, the subject matter of one or any combination of Examples 8-14 optionally includes adding a lead receptacle to the implantable medical device, wherein the lead receptacle is configured for insertion of an implantable lead.

Example 16 includes subject matter (such as an implantable medical device) or can optionally be combined with one or any combination of Examples 1-15 to include such subject matter, including a PCB including electronic circuit components mounted thereon, and an ID tag surface mounted on the PCB. The ID tag is metal ID tag that includes tungsten and alphanumeric characters are cut out of the metal plate.

In Example 17, the subject matter of Example 16 optionally includes glue between the ID tag and the PCB.

In Example 18, the subject matter of one or both of Examples 16 and 17 optionally includes the PCB being disposed in a hermetically sealed titanium metal case.

In Example 19, the subject matter of Example 18 optionally includes PCB and the ID tag being included in a leadless implantable medical device and the leadless implantable medical device excludes a liner within the metal case.

In Example 20, the subject matter of one or any combination of Examples 16-19 optionally includes the ID tag is mounted on the PCB without soldering the ID tag.

The non-limiting Examples can be combined in any permutation or combination. This summary is intended to provide an overview of the subject matter of the present application. It is not intended to provide an exclusive or exhaustive explanation of the invention. The detailed description is included to provide further information about the subject matter of the present patent application.

DETAILED DESCRIPTION

Figure 1:
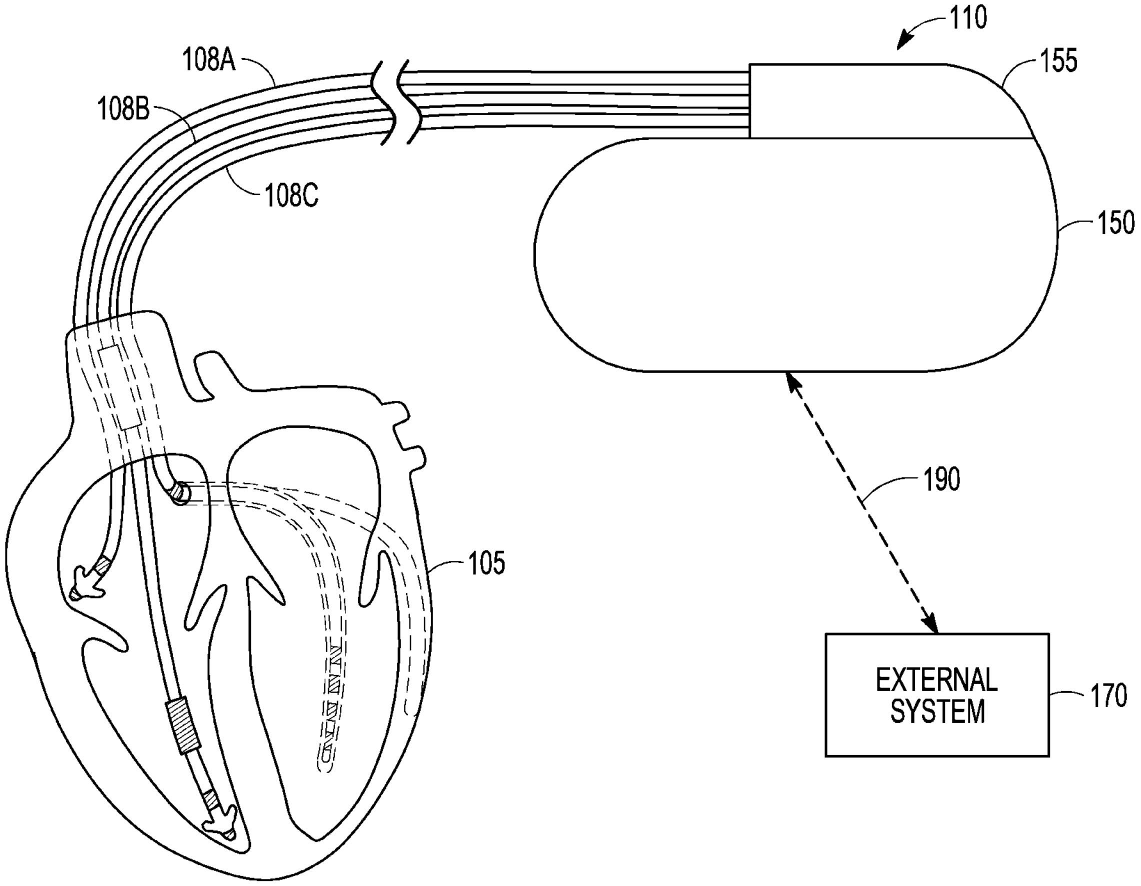
FIG. 1 is an illustration of portions of a system that uses an ambulatory medical device.

This document relates to techniques for including an identification tag with an ambulatory medical device. FIG. 1 is an illustration of portions of a system that uses an implantable medical device (IMD). Some examples of the IMD 110 include a pacemaker, a defibrillator, a cardiac resynchronization therapy (CRT) device, a combination of such devices, or a diagnostic-only device. The system also typically includes an IMD programmer or other external device 170 that communicates wireless signals 190 with the IMD 110, such as by using radio frequency (RF) or other telemetry signals.

The IMD 110 can be coupled by one or more conductive leads 108A-C to heart 105. The cardiac leads 108A-C in the example of FIG. 1 include a proximal end that is coupled to IMD 110 and a distal end, coupled by electrical contacts or "electrodes" to one or more portions of a heart 105. The electrodes typically deliver cardioversion, defibrillation, pacing, or resynchronization therapy, or combinations thereof to at least one chamber of the heart 105. The electrodes may be electrically coupled to sense amplifiers to sense electrical cardiac signals. Sensed electrical cardiac signals can be sampled to create an electrogram. An electrogram can be analyzed by the IMD and/or can be stored in the IMD and later communicated to an external device where the sampled signals can be displayed for analysis.

The cardiac leads 108A-C include right atrial (RA) lead 108A, right ventricle (RV) lead 108B, and a third cardiac lead 108C for placement in a coronary vein lying epicardially on the left ventricle (LV) via the coronary vein.

The IMD 110 includes a hermetically sealed metal housing or metal case 150 that houses electronic circuits and a header connector 155. Conductive leads (e.g., cardiac leads 108A-C) are connected to the IMD through the header connector 155. The header connector 155 includes lead receptacles for the cardiac leads 108A-C. The lead receptacles can be encapsulated in a mold material (e.g., an epoxy).

For implantable cardiac rhythm management devices, electrical signals sensed in the body and electrical signals delivered to the body need to pass through the hermetic seal. This is accomplished with feedthroughs. Feedthroughs are comprised of an electrical conductor, usually a pin, passing through insulating material and providing connection from circuitry internal to the case to a point external to the case (e.g., an electrode of a lead receptacle) while maintaining the hermetic seal. The header connector 155 provides the electrical connection between conductive leads and the feedthroughs.

Figure 2:
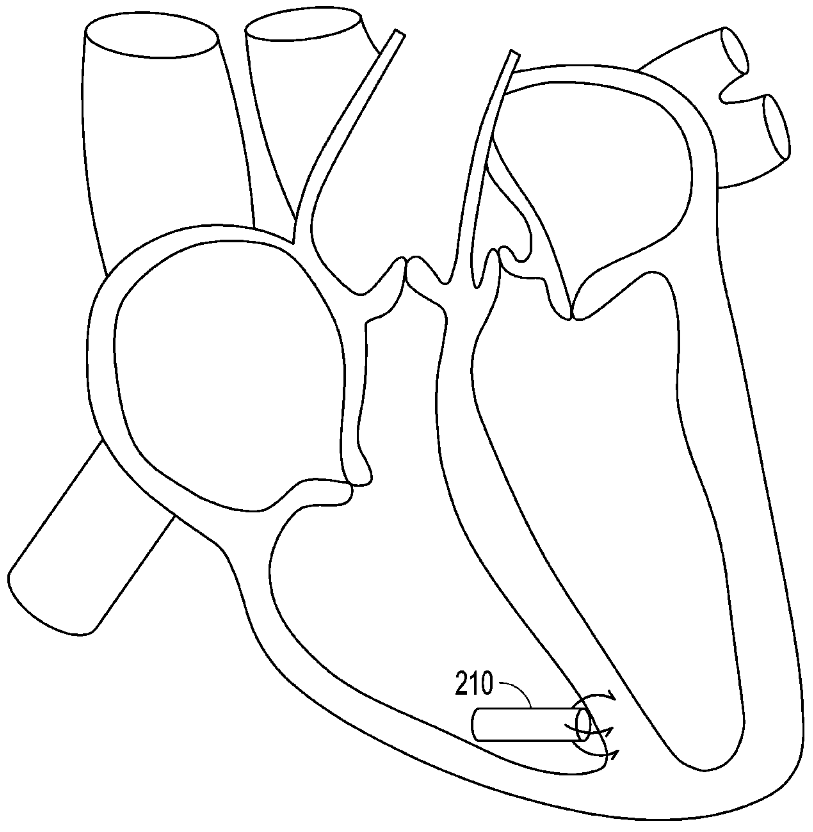
FIG. 2 is a view of another example of an ambulatory medical device.

FIG. 2 illustrates portions of another example of an IMD 210. The IMD 210 is leadless and is shown positioned at the endocardium within a ventricular chamber of a heart. The example of a leadless device shown in FIG. 2 has a rod or bullet shape and includes electrodes arranged along the cylindrical portion of the housing to provide electrical therapy to the heart.

Figure 3:
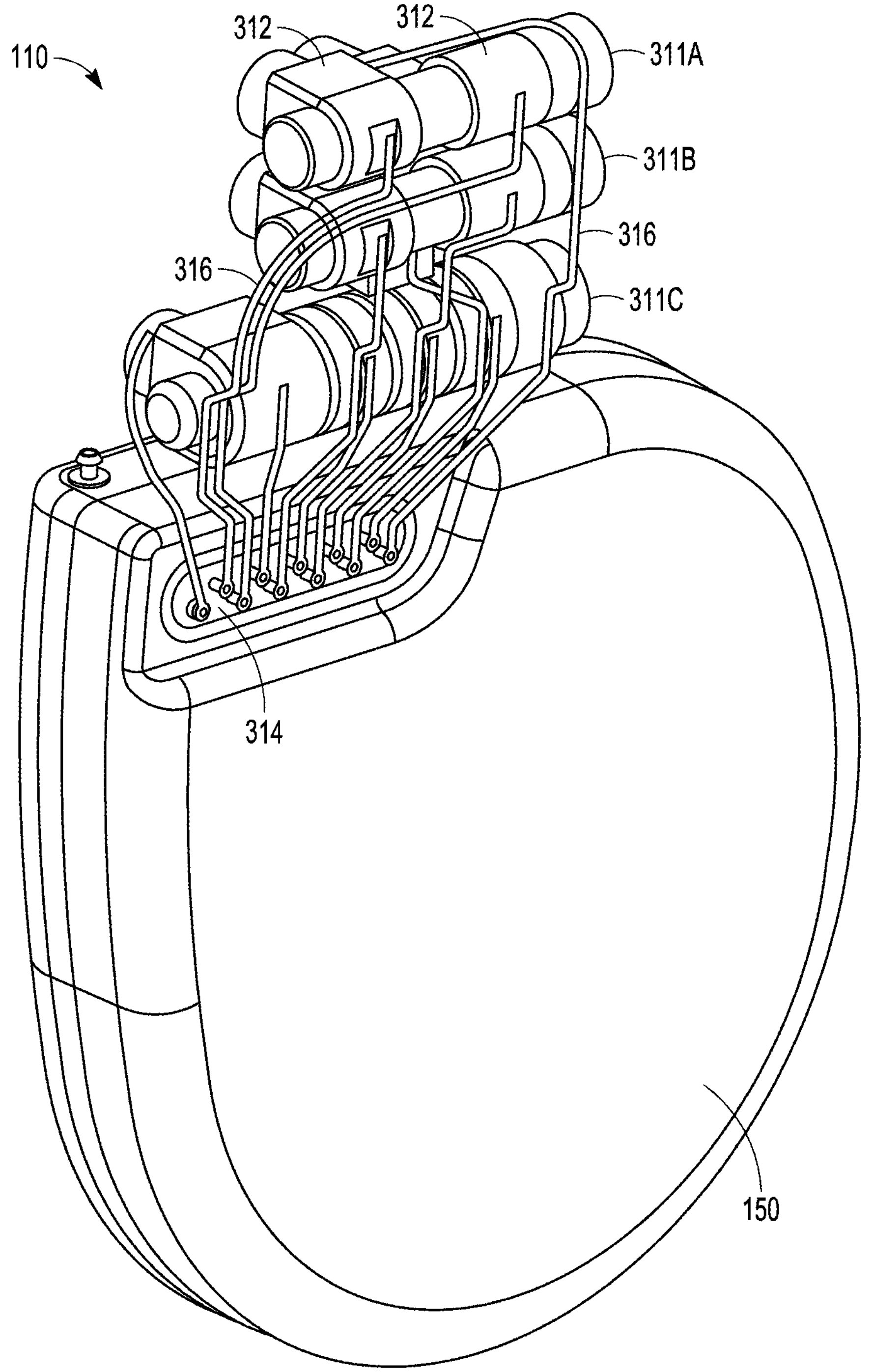
FIG. 3 is a view of another example of an ambulatory medical device.

FIG. 3 is a view of another example of an implantable medical device 110. The view shows the metal case 150 of the medical device and shows the header connector without the mold material to expose the lead receptacles. The header connector includes three lead receptacles 311A-C into which conductive leads can be inserted so that electrodes of the conductive leads contact electrodes 312 of the lead receptacles 311A-C. FIG. 3 also shows a feedthrough connector assembly 314 of the medical device 110. The feedthroughs are connected to the lead receptacles 311A-C by conductive wires 316.

It can be useful to uniquely identify a medical device. This may be done to reference the specific device to certain lot numbers of parts. An identification (ID) tag of an implanted device can be used to identify the manufacturer of the device or reference the device to records of its manufacturing process.

Figure 4:
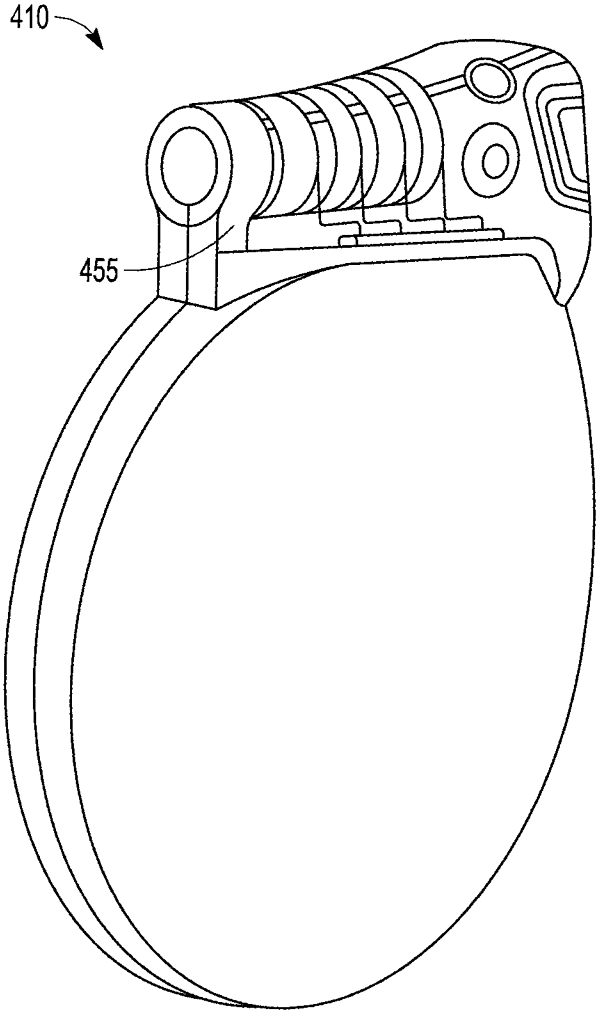
FIG. 4 is a view of still another example of an ambulatory medical device.

FIG. 4 shows an option for a location of a visual ID tag on an implantable medical device 410. An ID tag can be included in the header connector 455 of the medical device to provide a visual check of the medical device, but an ambulatory medical device may not always have a visible portion (e.g., a leadless implantable medical device) in which to place an ID tag. Also, a visual ID tag is not readable after the device is implanted.

Figure 5:
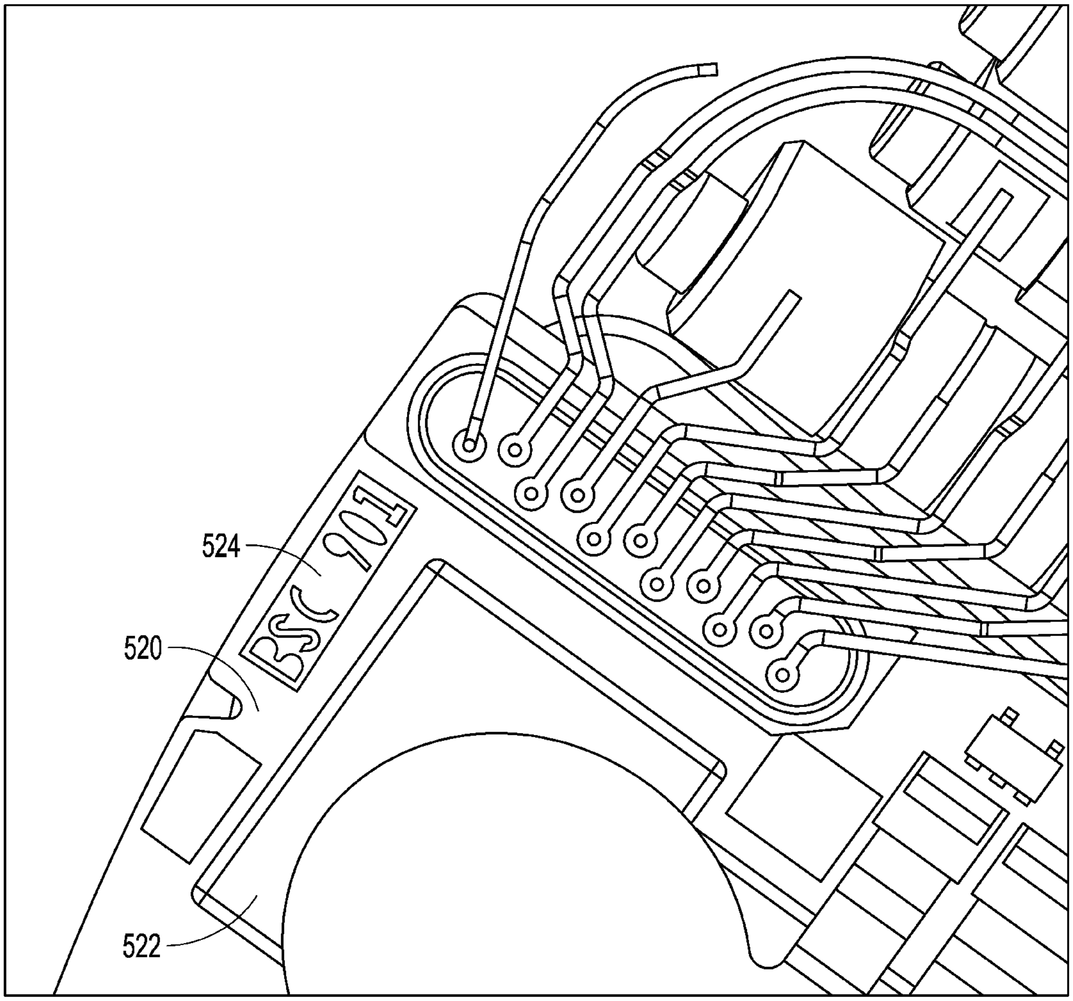
FIGS. 5 and 6 are views of an example of a portion of an implantable medical device.

FIG. 5 is another view of an example of a portion of an implantable medical device. The front plate of the metal case is removed to show the electronics inside the metal case. The Implantable medical device includes a printed circuit PCB 520. The PCB 520 can be made from FR4 epoxy. In certain examples, the PCB 520 includes ceramic. One or more circuit components 522 are mounted on the PCB 520.

The implantable device also includes an ID tag 524. The ID tag 524 can be surface mounted to the PCB 520. The ID tag 524 is readable by X-raying the medical device. To make the ID tag 524 readable, the ID tag 524 includes a metal that is much denser than the metal of the metal case of the implantable medical device. In some examples, the metal of the metal case is titanium and the metal of the ID tag 524 includes tungsten. Because tungsten is much denser than titanium, the ID tag 524 is readable when the implantable device is X-rayed.

Figure 6:
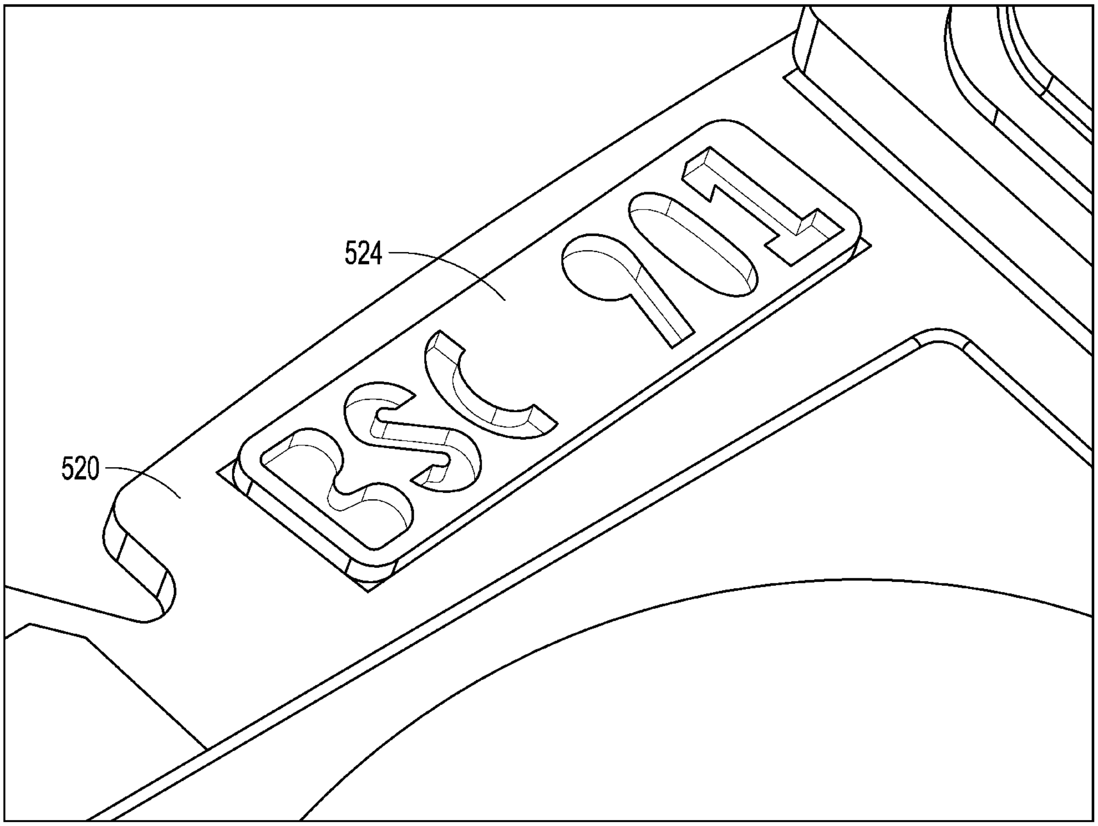

FIG. 6 is another view of the ID tag 524 and PCB 520. The ID tag 524 is made by cutting the alphanumeric characters into a tungsten plate. The result is metal plate that resembles a stencil. When the implantable medical device is X-rayed, the alphanumeric characters will be lighter than the metal plate. In some examples, raised alphanumeric characters of tungsten can be added to the PCB 520, but this is a more expensive option. The raised characters will be darker than the PCB in the X-rays.

Tungsten is not solderable, so the ID tag 524 is not soldered to the PCB 520. The ID tag 524 is attached to the PCB 520 using glue. For example, the ID tag 524 can be placed on the PCB 520 using a surface mount technology (SMT) component placement system and the ID tag 524 can be glue-dot surface mounted to the PCB 520. The re-flow process of the PCB 520 can be used to cure the glue underneath the ID tag 524 that holds the ID tag 524 to the PCB 520. Attaching the ID tag 524 to the PCB 520 with glue instead of solder also prevents solder flowing to fill in the characters of the ID tag 524 during the re-flow process. It also eliminates the added expense of adding a solderable metal (e.g., gold) to the tungsten ID tag 524 to make it solderable. A liner could be added to the metal case of the medical device and an ID tag could placed between the liner and the metal case. Attaching the ID tag 524 to the PCB 520 is technique that can be used in devices that do not have a liner.

Figure 7:
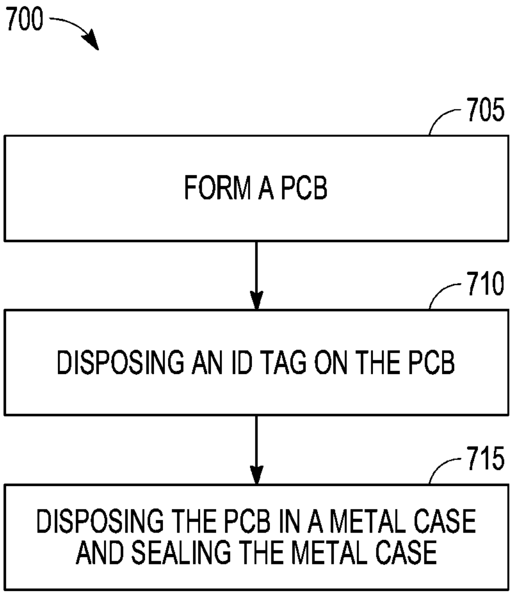
FIG. 7 is a flow diagram of an example of a method of manufacture of an ambulatory medical device.

FIG. 7 is a flow diagram of an example of a method 700 of manufacture of an implantable medical device, such as the implantable medical devices of FIGS. 1-3. The implantable device may include a lead receptacle (e.g., implantable medical device 110 in FIG. 3) or can be leadless (e.g., implantable medical device 210 in FIG. 2). At block 705, a PCB for the implantable medical device is formed (e.g., the PCB 520 of FIG. 5). The PCB includes electronic circuit components used in providing electrical energy as part of one or both of pacing therapy and defibrillation therapy. The PCB may be formed using FR4 epoxy or using a ceramic (e.g., aluminum oxide).

At block 710, an ID tag (e.g., ID tag 524 in FIG. 5) is disposed on the PCB. In some examples, the method 700 includes forming an ID tag that is a metal plate that includes tungsten and cutting alphanumeric characters out of the metal plate that uniquely identify the implantable medical device and may identify the manufacturer of the implantable medical device. Disposing the ID tag on the PCB can include surface mounting the ID tag on the PCB using glue. For example, the ID tag can be placed on the PCB using a pick-and-place machine and the ID tag can be glue-dot surface mounted on the PCB. The PCB may be re-flowed after the ID tag is attached to the PCB.

At block 715, the PCB assembly is disposed in a metal case of the implantable medical device and the metal case is hermetically sealed. The metal case is made from a metal that is less dense than the metal used in making the ID tag. For example, the metal case may be made of titanium. Because titanium is less than tungsten, the ID tag is readable within the metal case when the implantable medical device is X-rayed.

The devices described herein provide an ID tag that is readable when the device is X-rayed including after body implantation of the device.

Additional Description

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times. These computer-readable media can include, but are not limited to, hard disks, removable magnetic disks, removable optical disks (e.g., compact disks and digital video disks), magnetic cassettes, memory cards or sticks, random access memories (RAM's), read only memories (ROM's), and the like. In some examples, a carrier medium can carry code implementing the methods. The term "carrier medium" can be used to represent carrier waves on which code is transmitted.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. An implantable medical device, the device comprising:

a metal case composed of a first metal and having a hermetic seal configured to contain electronic components;

a printed circuit board (PCB) disposed within the metal case; and an identification (ID) tag arranged within the sealed metal case, wherein the ID tag is composed of a second metal denser than the first metal to be readable through the metal case by X-raying the implantable medical device to identify the implantable medical device after implantation in a patient, wherein the second metal is not solderable and is attached to the PCB during a re-flow process with glue to prevent solder from flowing into or over the ID tag during the re-flow process.

2. The device of claim 1, wherein the ID tag includes tungsten, and the metal case includes titanium.

3. The device of claim 1, wherein the ID tag is a metal plate with alphanumeric characters cut out of the metal plate.

4. The device of claim 1, wherein the PCB includes FR4 epoxy, and the ID tag is a metal ID tag that includes tungsten.

5. The device of claim 1, wherein the device is a leadless implantable medical device.

6. The device of claim 1, wherein the PCB is a ceramic material.

7. The device of claim 3, wherein the ID tag is attached to a surface of the PCB with glue during the re-flow process to prevent solder from flowing into the alphanumeric characters cut out of the metal plate during the re-flow process.

8. The device of claim 3, wherein the ID tag identifies the implantable medical device and a manufacturer of the implantable medical device.

9. The device of claim 3, wherein the ID tag identifies a manufacturing process of the implantable medical device.

10. The device of claim 1, comprising a header connector including at least one lead receptacle configured for insertion of an implantable lead, wherein the header connector is external to the metal case.

11. The device of claim 1, wherein the ID tag is glue-dot surface mounted to a surface of the PCB.

* * * * *